United States Patent [19]
Morgart et al.

[11] Patent Number: 5,242,595
[45] Date of Patent: Sep. 7, 1993

[54] BACTERIA REMOVAL BY CERAMIC MICROFILTRATION

[75] Inventors: James R. Morgart, Stillman Valley; James L. Filson, Rockford; Jeffery J. Peters, Loves Park, all of Ill.; Ramesh R. Bhave, Cranberry Township, Venango County, Pa.

[73] Assignee: U.S. Filter/Illinois Water Treatment, Inc., Warrendale, Pa.

[21] Appl. No.: 691,271

[22] Filed: Apr. 25, 1991

[51] Int. Cl.$^5$ .............................................. B01D 61/18
[52] U.S. Cl. .................... 210/636; 210/651; 210/500.26; 210/510.1
[58] Field of Search .............. 210/651, 500.26, 500.27, 210/500.25, 490, 496, 510.1, 257.2, 195.2, 321.69, 636; 427/230, 245, 246; 426/491

[56] References Cited

U.S. PATENT DOCUMENTS

| | | | |
|---|---|---|---|
| 2,984,628 | 5/1961 | Alexander et al. | 252/313 |
| 3,228,876 | 1/1966 | Mahon | 210/22 |
| 3,331,772 | 7/1967 | Brownscombe et al. | 210/23 |
| 3,344,928 | 10/1967 | Kraus et al. | 210/500 |
| 3,449,245 | 6/1969 | Johnson et al. | 210/23 |
| 3,497,394 | 2/1970 | Berger | 136/153 |
| 3,537,988 | 10/1970 | Marcinkowski et al. | 210/23 |
| 3,874,899 | 4/1975 | Miszenti et al. | 117/66 |
| 3,926,799 | 12/1975 | Thomas et al. | 210/23 |
| 3,944,658 | 3/1976 | Yoldas | 423/626 |
| 3,977,967 | 8/1976 | Trulson et al. | 210/23 |
| 3,993,751 | 11/1976 | Zinke | 424/128 |
| 4,060,488 | 11/1977 | Hoover et al. | 210/433 |
| 4,069,157 | 1/1978 | Hoover et al. | 210/433 |
| 4,078,112 | 3/1978 | Bibeau | 427/444 |
| 4,082,661 | 4/1978 | Aoki et al. | 210/40 |
| 4,168,229 | 9/1979 | Chambers | 210/23 |
| 4,251,377 | 2/1981 | Schleinitz | 210/510 |
| 4,356,215 | 10/1982 | Auriol et al. | 427/244 |
| 4,412,921 | 11/1983 | Leung et al. | 210/500.2 |
| 4,523,995 | 6/1985 | Pall et al. | 210/504 |
| 4,562,021 | 12/1985 | Alary et al. | 264/43 |
| 4,610,790 | 9/1986 | Reti et al. | 210/636 |
| 4,640,774 | 2/1987 | Garcera et al. | 210/323.2 |
| 4,652,376 | 3/1987 | Kumaoka | 210/694 |
| 4,698,157 | 10/1987 | Gillot | 210/496 |
| 4,724,078 | 2/1988 | Auriol et al. | 210/490 |
| 4,734,208 | 3/1988 | Pall et al. | 210/767 |
| 4,737,323 | 4/1988 | Martin et al. | 264/4.3 |
| 4,738,874 | 4/1988 | Berardo et al. | 427/244 |
| 4,837,028 | 6/1989 | Allen | 424/450 |
| 4,849,104 | 7/1989 | Garcera et al. | 210/323.2 |
| 4,865,742 | 9/1989 | Falletti | 210/637 |
| 4,876,100 | 10/1989 | Holm et al. | 426/491 |
| 4,909,942 | 3/1990 | Sato et al. | 210/651 |
| 4,927,571 | 5/1990 | Huang et al. | 264/4.3 |
| 4,929,406 | 5/1990 | Abe et al. | 264/45.5 |
| 4,983,423 | 1/1991 | Goldsmith | 427/230 |
| 5,032,265 | 7/1991 | Jha et al. | 210/257.2 X |

OTHER PUBLICATIONS

Abramson, D. et al, "Depyrogenation of a Parenteral Solution by Ultrafiltration", *Journal of Parenteral Science and Technology*, vol. 35, No. 17 Jan.–Feb. 1981, pp. 3–7.

Baggerman, C. et al, "Endotoxin Removal From Large-Volume Parenterals by Various Adsorbents", *International Journal of Pharmaceutics*, 27 (1985), pp. 17–27.

Bergauer, R. G. et al, "The Removal of Pyrogens from Injection Preparations Containing Organic Solvents", *Technical Information*, pp. 86–87.

*Biopharm*, Oct. 1989, vol. 2, #9 (Advertisement).

Chervan, M., *Ultrafiltration Handbook*, Technomic Publishing, Lancaster, PA, (1986), pp. 246–250.

(List continued on next page.)

*Primary Examiner*—Frank Spear
*Attorney, Agent, or Firm*—Douglas G. Glantz

[57] ABSTRACT

The method of the present invention for separating bacteria includes passing a bacteria-containing liquid through a plural-coated-sintered inorganic membrane on a larger pore size inorganic ceramic support. By plural-coated-sintered is meant at least two sintered coatings of substantially similar pore size. The membrane on a ceramic support preferably includes a porous double-coated sintered ceramic oxide membrane on an alpha-alumina support.

20 Claims, 1 Drawing Sheet

OTHER PUBLICATIONS

Gerba, Charles P. et al, "Pyrogen Control by Depth Filtration", *Pharmaceutical Technology*, Jun. 1980, pp. 83-89.

Gillot, J et al, "New Ceramic Filter Media for Cross-Flow Microfiltration and Ultrafiltration", *Avril* 1986, pp. 1-8.

Giorgio, Robert J., "Considerations in the Design of Hot Circulating Water-for-Injection Systems", *Pharmaceutical Technology*, Dec. 1978, pp. 19-25.

Henderson, Lee W. et al. "Successful Production of Sterile Pyrogen-Free Electrolyte Solution by Ultrafiltration", *Kidney International*, vol. 14 (1978) pp. 522-525.

Leahy, Timothy J. et al, "Validation of Bacterial-Retention Capabilities of Membrane Filters", *Pharmaceutical Technlogy*, Nov. 1978, pp. 65-75.

McGregor, W. Courtney, "Selection and Use of Ultrafiltration Membranes", *Membrane Separations in Biotechnology*, Marcel Dekker, Inc., New York, pp. 1-36.

Nelsen, Lita L., "Removal of Pyrogens form Parenteral Solutions by Ultrafiltration" *Pharmaceutical Technology*, May 1978, pp. 46, 48, 49, and 80.

Olson, Wayne P., "How to Evaluate Microporous Filtration of Water", *Industrial Water Engineering*, Jan.-/Feb. 1979, pp. 20-25.

SFEC Brochure, 4 pages.

"Self-Repairing Membranes Hold Promise in Desalting Brackish Water", *Chem. and Eng. News*, Dec. 19, 1966, page 47.

Wilke, H. "Filtration von Injektionspraparaten im Pharmazeutischen Betrieb", *Pharm. Ind.* 18, pp. 426-440.

Wolber, P. et al, "Depyrogenation of Pharmaceutical Solutions by Ultrafiltration: Aspects of Validation", *Pharmaceutical Technology*, Sep. (1987), 6 pages.

Woog, H. et al, "Sterilfiltration und Entpyrogenisierung von parenteralen Arzneimitteln mit neuen asbestfreien Tiefenfiltern", *Pharm. Ind.*, 39, No. 12, pp. 1261-1266.

Zimmerman, F. et al, "Pyrogen Elimination form Parenteral Medicines by Means of Molecular Filteration", *Drugs Made in Germany*, 19, (1976), pp. 123-128.

Technical Report No. 7, Parenteral Drug Association, Inc., 1986, Chapters 1-14.

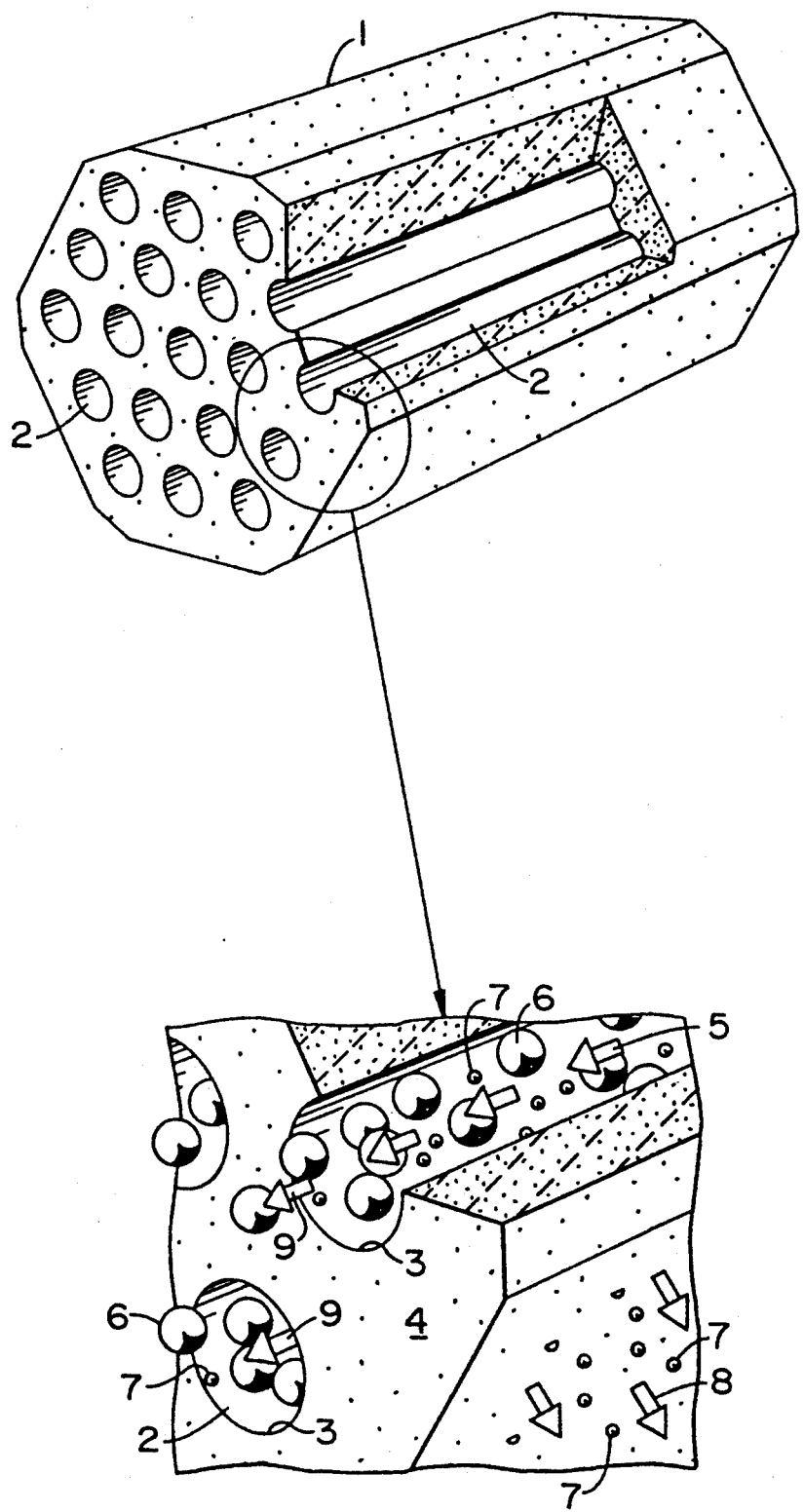

BACTERIA REMOVAL BY CERAMIC MICROFILTRATION

BACKGROUND OF THE INVENTION

This invention relates to bacteria removal by ceramic filtration.

Bacteria removal from solutions by filtration was recognized as early as the 19th century by Pasteur.

Bacteria are living organisms often composed of a single cell in the form of straight or curved rods (bacilli), spheres (cocci), or spiral structures. Their chemical composition is primarily protein and nucleic acid. Bacteria can be classified by particle sizes in the range of about 0.2 to 2.0 microns.

Microfiltration membranes are used for separation processes over a range of filtration size exclusion of generally from about 500Å or 0.05 micron to about 1 to 2 microns. In the context of filtration separations over an entire spectrum of small particle separation processes, reverse osmosis extends from about 1 to 10Å to 20Å, ultrafiltration from about 10Å to 2000Å, microfiltration from about 500Å or 0.05 micron to about 2 microns, and macroparticle filtration from about 1 to 2 microns and up.

Microfiltration can be an effective means of bacteria removal because the bacteria of interest are larger than 0.2 micron.

The membrane filters suggested for bacteria removal in early attempts were made using 0.45 micron and 0.80 micron organic membranes. Later, organic membranes of 0.22 micron pore size were introduced to filter pseudomonas-like organisms.

Microfiltration membranes concentrate particulate products and are capable of separating microemulsions. Through concentration, the solids material larger than the rate pore size of the filter is retained by the filter in a retentate while water and low molecular weight solutes including salts, alcohols, or others, pass through the membrane as a permeate. The concentration operation can be limited by a buildup is called the concentration polarization layer and results in significant resistance to filtration flow.

Prior microfiltration methods for bacteria removal from liquids were identified with organic polymer structures with pore sizes larger than ultrafiltration membranes but smaller than the macroparticle filters.

Life sciences filtration applications, including bacteria removal, typically produce a slime on the polymeric membrane, including a film layer which sets up in cross-flow ultrafiltration. Polymeric membranes are susceptible to this buildup of slime and often are limited in their method of cleanup. The polymeric membrane also can be degraded by high temperatures or concentrated corrosive chemicals, e.g., such as acids or bases which otherwise would readily clean the membrane.

Polymeric membranes have this drawback not only in cleanbility but also in initial sterilization. To deliver bacteria-free product, the filter must be initially sterilized. The membrane should be sterilizable to eliminate colony-forming bacteria on the membrane structure. Further, the polymeric materials typically cannot be sterilized with very high heat, with high pressure saturated steam, or repeated cycles of low pressure steam. The same factors attributable to polymeric membranes as drawbacks for initial cleaning also apply to regeneration of the polymeric systems.

It is an object of the present invention to provide a method for sterilizing a liquid by removing bacteria through a filter which can be chemically cleaned initially and on repetitive regeneration.

It is a further object of the present invention to provide a method for removing bacteria through a filter which can be steam sterilized initially and on repetitive regeneration.

It is a further object of the present invention to provide a filter for removing bacteria from a liquid which can be used over a long period and through numerous regeneration cycles.

It is yet another object of the present invention to provide a method for removing bacteria from a liquid through a filter having high permeability.

These and further objects of the present invention will become apparent from the detailed description which follows.

INTRODUCTION TO THE INVENTION

Asymmetric ceramic filters provide media for microfiltration and ultrafiltration separation processes. These ceramic filters today are becoming recognized for their excellent structural bonding and integrity and are rapidly extending the fields of filtration applications to separations processes performed under extreme conditions of pressure, temperature, and pH.

"New Ceramic Filter Media for Cross-Flow Microfiltration and Ultrafiltration" by J. Gillot et. al. of the Ceramic Membranes Department of SCT in Tarbes, France, as published in *Filtra* 1984 *Conference*, Oct. 2–4, 1984, (April, 1986) presents alumina membrane-on-support filter media composed of a macroporous support with ceramic membrane layered on multi-channels through the support over channel diameters of 4 or 6 mm. Microfiltration membranes are presented with average pore diameters ranging from 0.2 micron to 5 microns, and ultrafiltration membranes are presented with average pore diameters ranging from 40Å to 1000Å. The membranes on support elements are assembled in modules with filtration surface areas of 0.01 to 3.8 m$^2$. The Gillot et. al. publication points out characteristics for a support composition of alpha-alumina and for microfiltration membranes composed of alpha-alumina and for ultrafiltration membranes of gamma-alumina.

SUMMARY OF THE INVENTION

The method of the present invention for separating bacteria includes passing a bacteria-containing fluid through a plural-coated-sintered inorganic membrane on a larger pore size inorganic ceramic support. By plural-coated-sintered is meant at least two sintered coatings of substantially similar (no more than 50% larger) nominal pore size. The membrane on a ceramic support preferably includes a porous double-coated sintered ceramic oxide membrane on an alpha-alumina support.

BRIEF DESCRIPTION OF THE DRAWING

The sole Figure shows a schematic representation of a membrane on ceramic support for cross-flow microfiltration in accordance with the present invention.

DETAILED DESCRIPTION OF A PREFERRED EMBODIMENT

Pore size and membrane integrity are critical in a membrane's ability to remove bacteria and sterilize by filtration. Physical tests to determine pore size and membrane integrity include bubble point, forward-flow, diffusive-flow, mercury intrusion, pore size distribution, and particle-passage methods. Bubble point tests provide tests for integrity of the membranes as well as pore size determination.

It has been found that the method of the present invention provides bacteria removal through a plural-coated-sintered ceramic membrane on ceramic support. Prior ceramic membranes of similar nominal pore size and thickness without the plural-coated-sinter do not filter out all bacteria of a size larger than the membrane pore size. The present invention provides bacteria removal combined with advantages of high permeability throughout an extended operating time while providing excellent regenerability through the method employing the plural-coated-sintered membrane on ceramic support of the present invention.

Bacteria are extremely small (usually 0.2 to 2.0 microns in diameter) and relatively simple microorganisms. Bacteria are further defined as life sciences substances which are characterized as any of a large group of microscopic plants constituting the class Schizomycetes having spherical round, rod-like, spiral, or filamentous single-celled or non-cellular bodies that are often aggregated into colonies, are enclosed by a cell wall or membrane, usually lack fully differentiated nuclei, and are often motile by means of flagella, reproducing by fusion, by the formation of asexual resting spores or, in some higher forms, by conidia or by imperfectly understood sexual processes, living on soil, water, organic matter or the live bodies of plants and animals, and being autotrophic, saprophytic, or parasitic in nutrition and important to man because of their chemical effects (as in nitrogen filtrations, putrefaction, and various fermentations) and as pathogens.

The bacteria referred to in this detailed description of the process of the present invention include bacteria having a particle size of about 0.2 micron up to about 2.0 microns.

Pseudomonas diminuta provides the representative characteristics for bacteria removal investigations. Pseudomonas diminuta is a small asporogenous gram-negative rod having polar flagella. Pseudomonas diminuta forms colonies of about 1 to 2 mm in diameter on trypticase soy agar after incubation for about 48 hours at 30° C.

The method of the present invention includes using plural-coated-sintered membranes having nominal pore sizes such that the pore size of a second or subsequent sintered coating is substantially similar to a first sintered coating. By similar is meant the nominal pore size of the second sintered coating is no larger than 1.5 times the nominal pore size of the first sintered coating. By nominal pore size is meant average pore size, e.g., such as about 0.2 micron, including more than about 90% of the pore sizes are within the range of about plus or minus 10% of the nominal pore size, e.g., such as plus or minus 0.02 micron in the case of 0.2 micron nominal pore size. A first sintered coating having a nominal pore size of the 0.2 micron would be capable of combination in the membrane of the present invention with a second sintered coating of nominal pore size no larger than about 0.3 micron.

The method of the present invention for bacteria removal preferably uses a membrane on a support material where the support preferably comprises an alpha-alumina multi-layer support. The alpha-alumina support is a multi-layer structure comprising a sublayer, e.g., such as a sublayer of 0.2 micron pore diameter preferably about an average of 25 microns thick, integrally bonded to support a microfiltration layer, e.g., a membrane layer which is further supported on a second sublayer, e.g., of about 0.8 micron pore diameter preferably of about an average of 30 to 50 microns thickness, on the other side of the first sublayer. This structure is further supported on a porous support which has a pore diameter of about 10 to 15 microns and a thickness of about 1.5 to 2 mm.

The plurality coated-sintered (or multiple two or more complete layer) ceramic membrane can be made of ceramic oxide materials, e.g., such as alumina or zirconia. The present invention can be illustrated in one perspective by the preferred embodiment for manufacturing the plural-coated-sintered (two complete sintered layers) ceramic membrane of the present invention.

The production of double layer microporous alumina or zirconia is a multi-step process. First, a single layer 0.2 micron composite membrane structure is obtained. Then, a second membrane of substantially similar pore size, i.e., in this case no larger than 0.3 micron which is no larger than 1.5 times the pore size of the first coating, is deposited on top of the 0.2 micron layer under substantially similar operating conditions to those used in the synthesis of the 0.2 micron layer.

Composite alumina or zirconia membranes are synthesized by the slipcasting process. In this process, a porous support is made first (10–15 micron diameter pores). This provides a rigid structure with a relatively large pore size for slip deposition. Since particle size and pore size are directly related, the slip used as the membrane precursor contains well dispersed particles of uniform size.

After treatment with a peptizing agent such as an acid and optionally with a viscosity modifier, the slip is deposited onto the porous support by the slipcasting process. This is a filtering process based on the capillary pressure drop created by the contact of the slip with the support. This pressure drop forces the dispersion medium (e.g., water) to flow into the dry pores of the support while the slip particles are retained and concentrated at the surface forming a thin membrane.

The membrane precursor is then dried and calcined to provide the required pore size and the needed bonding between the membrane and the support. The processing conditions are carefully controlled to avoid cracks which can occur due to shrinkage and upon calcining. This method is used to slipcast first the 0.8 micron layer on the 10–15 micron porous support. A second layer with a pore diameter of 0.2 micron is deposited on top of the 0.8 micron layer.

This process is used in the manufacture of the composite microporous single layer 0.2 micron $Al_2O_3$ membranes. The thickness of a standard 0.2 micron layer is in the range 20–30 microns. The intermediate 0.8 micron layer has a thickness of about 30–50 microns. The porosity of each layer ranges between 35 to 50%, including porous support.

The advantage of a double layer membrane lies in the fact that small defects in the standard 0.2 micron layer allow a few bacteria to pass. A second substantially similar layer on top of the standard 0.2 micron layer eliminates (drastically reduces) the probability of bacterial leakage. This has now been experimentally established as shown in the Examples described.

A specific example of a double-coated membrane on support is available from Societe Des Ceramiques Techniques (SCT) in Tarbes, France and is referred to as STERILOX# ceramic membranes.

Each finished membrane is tested for compliance with integrity specifications by means of a bubble point test used to check for possible point defects. For this test, the supported membrane is enclosed in a suitable container and is immersed in ethanol. Nitrogen gas is injected into the membrane side of the container. The pressure at which nitrogen gas bubbles appear on the support surface of the unit is used to calculate the size of possible defects.

The sterilization method of the present invention includes passing the bacteria-containing liquid over the plural-coated-sintered membrane in a cross-flow or tangential flow over the membrane. By cross-flow or tangential flow is meant that the feed flow is axially channeled and essentially perpendicular to the flow of permeate through the support as shown in the schematic of the sole Figure.

Referring to the sole Figure, a schematic diagram is shown for cross-flow microfiltration in accordance with the method of the present invention using the ceramic membrane on ceramic support. Ceramic support 1 of alpha-alumina in accordance with the present invention has multi-channels 2 incorporated in the monolithic support material. The channels can be 4 or 6 mm in diameter and are set up in multiple number, e.g., 19 channels per element. A membrane on support is formed inside of the axially oriented channels. Double membrane coating 3 provides the ceramic plural-coated-sintered membrane 3 on alpha-alumina support material 4. Feed stream 5 containing bacteria 6 and water 7 is passed into the channels or lumens 2. A back pressure is applied to the feed stream 5 and a permeate stream 8 is passed through the membrane 3 and support material 4 and exits as permeate stream 8. The permeate in this case is primarily water 7. Retentate stream 9 exits the channels and includes bacteria 6 and water 7. The membrane 3 preferably has a total depth of about 40-60 microns.

It has been found that the method in accordance with the present invention separates bacteria from a liquid to form a sterilized fluid. By sterilized fluid is meant no detectable bacteria passing, with a challenge level of $10^7$ org/cm$^2$. The methods for detecting bacteria include incubation on a suitable nutrient media for a specified time and visually counting bacteria colonies. To achieve an effective utilization of the bacteria removal process, the initial membrane on support should be sterilized prior to operation of the method of the present invention. Sterilization can be accomplished by thermally or chemically sterilizing the filter apparatus.

The method of the present invention can be described in functional terms also as, for example, by purifying a liquid to remove bacteria including passing a bacteria-containing liquid through a ceramic membrane having a flux higher than about 1100 L/hr·m$^2$ at one bar trans-membrane pressure to remove bacteria without substantial fouling of the membrane through a run time of several hours. It has been found empirically through experimental observation and testing that the method provides unexpectedly superior separations characteristics of high flux and limited fouling as shown by the observation of flux through the ceramic membrane on ceramic support in the method of the present invention.

The superior characteristics will be described further in the Examples which follow.

A double coated-sintered ceramic membrane having a nominal pore size of about 0.2 micron was evaluated according to the HIMA Guidelines for Evaluation of Sterilizing Filters. Test organisms were pseudomonas diminuta, ATCC 19146 (for 0.2 micron membrane challenge). Media were (1) saline lactose broth (SLB); (2) soybean casein digest agar; and (3) soybean casein digest broth. For the HIMA challenge level, filters to be tested were challenged with a suspension of test organism at a concentration of $10^7$ org/cm$^2$ of effective filtration area. Total filtration area to be tested was 2000 cm$^2$. Organisms used in the test required to achieve $10^7$ org/cm$^2$ was at least $10^{10}$ organisms.

Pseudomonas diminuta ATCC 19146 challenge organism was prepared in the following manner. P. diminuta was inoculated trypticase soy broth (TSB) and incubated for 18-24 hours at 30±2° C. Three (3) liters of saline lactose broth (SLB) were inoculated with approximately 75 ml of the P. diminuta in TSB. The SLB was incubated for 24 hours at 32°-35° C.

After placement of the ceramic membrane filter into a housing, the filter and housing were steam sterilized by autoclaving. Appropriate tubing, connectors, filters, and reservoirs were steam or EtO sterilized and cooled to room temperature before use.

Approximately five (5) to eight (8) L of sterile water were filtered through the system to ensure a wet filter membrane before challenge. A pressure hold test was performed at approximately 7 bar by connecting the pressure supply directly to the filter. After the flow stopped, the drops expelled were counted over a period of one minute. Results were recorded.

Each test filter was then challenged with approximately $10^7$ org/cm$^2$ of effective filtration area (EFA). A sample of the filtrate was taken during the test. Samples of 5 ml, 1 ml, and $10^1$, $10^2$, and $10^3$ were plated directly from the filtrate. Each was plated in duplicate and over-poured with plate count agar. All the filtrate was filtered through a 0.45 micron membrane which was then aseptically placed upon a sterile plate count agar surface and incubated at 30±2° C. for three (3) to seven (7) days. A post microbial challenge pressure hold test was performed as in the preceding paragraph.

After appropriate incubation and enumeration of the plates, the log reduction value was calculated according to the following formula:

$$LRV = \text{Log } 10 \frac{\text{Number Organisms in Challenge}}{\text{Number Organisms in Filtrate}}$$

When the filtrate is sterile, one (1) is substituted in the denominator and the LRV is expressed as greater than the calculated values.

The following elements were tested by HIMA challenge and passed, with no organisms passing through the membrane when tested per the standard HIMA protocol. Bubble point tests carried out on these elements prior to HIMA challenge indicated that the membrane surfaces were integral and contained no significant defects.

TABLE I

| Element No. | Log Reduction Value |
|---|---|
| 399 | 11.0 |
| 400 | 10.6 |
| 401 | 10.4 |

TABLE I-continued

| Element No. | Log Reduction Value |
|---|---|
| 402 | 10.3 |
| 403 | 11.0 |
| 404 | 10.4 |
| 405 | 10.7 |
| 406 | 10.4 |
| 407 | 11.4 |
| 408 | 10.9 |
| 409 | 10.9 |
| 410 | 10.6 |
| 411 | 11.0 |
| 412 | 10.5 |
| 413 | 10.2 |
| 414 | 10.7 |
| 415 | 11.0 |
| 416 | 10.3 |
| 417 | 10.3 |
| 418 | 10.3 |

The following elements were tested by HIMA challenge and failed, with one or more organisms passing through the membrane when tested per the standard HIMA protocol. Bubble point tests carried out on these elements prior to HIMA challenge indicated that the membrane surfaces were not integral and contained significant defects.

TABLE II

| Element No. | Log Reduction Value |
|---|---|
| 466 | 8.4 |
| 468 | 8.8 |

While the invention has been described in terms of preferred embodiments, the claims appended hereto are intended to encompass all embodiments which fall within the spirit of the invention.

What is claimed is:

1. A method of separating bacteria comprising passing bacteria-containing fluid through a plural-coated-sintered ceramic membrane on ceramic support, the membrane comprising at least a first sintered membrane formed by sequential layering and a subsequent sintered coating.

2. A method as set forth in claim 1 wherein said ceramic support comprises a porous sintered alpha-alumina support.

3. A method as set forth in claim 2 wherein said membrane comprises alpha-alumina.

4. A method as set forth in claim 2 wherein said membrane comprises zirconia.

5. A method as set forth in claim 2 wherein said membrane has a first sintered coating of nominal pore size less than or equal to about 0.22 micron and a second sintered coating of nominal pore size no larger than 0.3 micron.

6. A method as set forth in claim 5 wherein said passing bacteria-containing fluid comprises a cross-flow or tangential flow over said membrane.

7. A method as set forth in claim 6 further comprising an initial thermal sterilization of said membrane.

8. A method as set forth in claim 7 wherein said liquid comprises water.

9. A method as set forth in claim 8 wherein said bacteria-containing liquid comprises water containing bacteria having a particle size of about 0.2 to 2.0 microns.

10. A method as set forth in claim 9 wherein said bacteria have a particle size of about 0.22 to 0.3 micron.

11. A method of purifying a fluid to remove bacteria comprising passing bacteria-containing liquid through a ceramic membrane having a permeability higher than about 1100 L/hr m$^2$·bar to remove bacteria at a filtering capability of $10^7$ org/cm$^2$ bacteria per effective filter area without substantial fouling of the membrane.

12. A method as set forth in claim 11 wherein said fluid comprises liquid.

13. A method as set forth in claim 12 wherein said ceramic membrane has a nominal pore size in the range of about 0.18 to 0.22 micron.

14. A method as set forth in claim 13 wherein said passing comprises a cross-flow or tangential filtration.

15. A method as set forth in claim 16 wherein said separation comprises at least a 10 LOG reduction in bacteria in said liquid.

16. A method as set forth in claim 14 wherein said bacteria separation comprises forming a permeate of sterilized liquid.

17. A method as set forth in claim 16 wherein said liquid comprises water and said bacteria comprise life sciences substances having particle sizes in the range of about 0.2 to 2.0 microns.

18. A method of separating bacteria comprising:
 (a) providing a sterilized, membrane of porous plural-coated-sintered ceramic having two or more substantially similar sintered coatings on alpha-alumina support by treating said membrane on support with saturated steam; and
 (b) passing bacteria-containing water by cross-flow or tangential filtration over and through said plural-coated-sintered ceramic membrane on alpha-alumina support to separate bacteria and form a sterilized permeate.

19. A method as set forth in claim 18 wherein substantially similar sintered coatings comprise one sintered coating having a nominal pore size no smaller than about one-half the nominal pre size of an underlying sintered coating.

20. A method of separating bacteria comprising passing bacteria-containing fluid in a cross flow or tangential flow direction through a plural-coated-sintered ceramic membrane on a porous sintered alpha-alumina support, wherein said membrane comprises at least a first sintered coating of nominal pore size of less than or equal to about 0.22 micron formed by sequential layering and a second sintered coating of nominal pore size no larger than about 0.3 micron, to form a sterilized fluid.

* * * * *